US00PP29236P3

(12) United States Plant Patent
Olesen et al.

(10) Patent No.: US PP29,236 P3
(45) Date of Patent: Apr. 17, 2018

(54) *CLEMATIS* PLANT NAMED 'EVIPO100'

(50) Latin Name: *Clematis viticella*
Varietal Denomination: Evipo100

(71) Applicants: Mogens Nyegaard Olesen, Fredensborg (DK); Raymond J. Evison, St. Sampsons (GB)

(72) Inventors: Mogens Nyegaard Olesen, Fredensborg (DK); Raymond J. Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/330,279

(22) Filed: Sep. 6, 2016

(65) Prior Publication Data

US 2018/0070513 P1 Mar. 8, 2018

(51) Int. Cl.
*A01H 5/02* (2006.01)

(52) U.S. Cl.
USPC ..... Plt./228

(58) Field of Classification Search
USPC ..... Plt./228
CPC ..... A01H 5/02
See application file for complete search history.

(56) References Cited

PUBLICATIONS http://www.notesontheroad.com/Ying-s-Links/Chelsea-Flower-Show-2013-30-glorious-new-plants-on-show.html; May 1, 2013; 23 pages.*

* cited by examiner

*Primary Examiner* — Kent L Bell

(57) ABSTRACT

A new *Clematis* plant with a compact growth habit, profuse, light blue flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification: Genus: *Clematis*. Species: *viticella*.

Variety denomination: 'Evipo100'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2000 and the resulting seeds were planted the following winter in a controlled environment in Guernsey, Channel Islands, United Kingdom. The new variety named 'Evipo100' originated as a single seedling from the stated cross.

The new *clematis* plant may be distinguished from its female seed parent and male pollen parent by the following characteristics. The female seed parent has X tepals while the new variety has light blue tepals. The male seed parent has X tepals while the new variety has light blue tepals.

The objective of the hybridization of this *clematis* plant was to create a new and distinct variety for nursery culture with unique qualities such as:

1. Uniform and abundant light blue flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo100' was selected by Mogens N. Olesen and Raymond J. Evison in their *clematis* development program in the Channel Islands, United Kingdom in 2001. Asexual reproduction of 'Evipo100' by means of vegetative cuttings and traditional layering was first performed by Mogens N. Olesen and Raymond J. Evison in the nursery during the summer of 2001. This initial and subsequent asexual propagations have demonstrated that the characteristics of 'Evipo100' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo100'. Specifically illustrated in the drawing are open flower viewed from above, a branch showing attachment of flower buds and open flower, tepals detached, reproductive flower parts, and a compound leaf. Plants shown are 2 years of age.

DETAILED DESCRIPTION OF THE VARIETY

The following is a detailed description of 'Evipo100', as observed in its growth throughout the flowering period in Marion County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo019' described and illustrated in U.S. Plant Pat. No. 16,069 are compared to 'Evipo100' in Chart 1.

CHART 1

| | 'Evipo100' | 'Evipo019' |
|---|---|---|
| Flower diameter | 90 mm | 90 to 120 mm |
| Tepal upper surface upon opening | Violet Group 85A, with light intonation of Red-Purple Group 73B | Violet Group N88B |
| Tepal count | 11 | 8 |

FLOWER AND FLOWER BUD

Blooming habit: Recurrent. The natural flowering period is generally from May to September.

Flower bud:

*Size*.—Normally 30 mm in length. Bud diameter is 14 mm.

*Bud form*.—Elliptic.

*Bud color*.—At ¼ opening Yellow-Green Group 147D.

*Texture*.—Highly pubescent.

Pedicel:

*Surface texture*.—Smooth.

*Length*.—On average 25 mm in length with 3 mm diameter.

*Color*.—Yellow-Green Group 147D.

*Strength*.—Moderately strong.

Receptacle:

*Surface texture*.—Lightly pubescent.

*Shape*.—Broad funnel.

*Size*.—2 mm (h)×2 mm (w).

*Color*.—Yellow-Green Group 147D.

Flower arrangement:

*Location on vine*.—New and old growth.

*Borne*.—7 to 9 flowers per branch, borne along axillary and terminal flower buds.

Flower bloom:

*Size*.—On average, flowers are 90 mm in diameter and 20 mm in depth.

*Profile*.—Open flowers are flat.

*Fragrance*.—None.

*Lasting quality*.—Flowers normally remain up to 10 days on the plant.

Tepals:

*Tepal color*.—Upon opening, and after opening, the upper surface is Violet Group 85A, with light intonation of Red-Purple Group 73B. The lower surface is Violet Group 85B, with central bar of White Group 155A.

*Quantity*.—Normally 11 tepals.

*Size*.—42 mm in length by 27 mm wide.

*Shape*.—Individual tepal shape is ovate. The tepal apex is acute. The tepal base is typically acute.

*Apex recurvature*.—None.

*Tepal cross section*.—Reflexed somewhat.

*Margins*.—Entire. Medium undulations of margin observed.

*Persistence*.—Tepals drop off cleanly.

Reproductive organs:

*Arrangement*.—Open.

*Pollen*.—None observed.

*Anthers*.—Size: 5 mm in length. Color: Greyed-Yellow Group 160C. Quantity: On average, 35.

*Filaments*.—Color: White Group N155D. Length: 6 mm.

*Pistils*.—Quantity: On average, 20.

*Stigmas*.—Level in location relative to the length of the filaments and the height of the anthers.

*Styles*.—Color: White Group 155A. Length: 11 mm.

PLANT

Plant form: Climbing and spreading.

Plant growth: Moderately vigorous.

Size: Seasons growth attains 100 cm in height. Average spread is 50 cm.

Stems:

*Color*.—Juvenile stems are Yellow-Green Group 144A. Mature stems are Yellow-Green Group and Greyed-Orange Group 166A.

*Internodes*.—On average, 35 mm between nodes.

*Length*.—Normally 25 to 30 cm from the base of the plant to the flowering portion of the stem.

*Diameter*.—Normally 4 mm.

*Texture*.—Mature stems are generally ribbed.

Plant foliage:

*Leaf characteristics*.—Deciduous.

*Arrangement*.—Trifoliate.

*Leaf size*.—Compound leaves are normally 100 mm (l)×90 mm (w). Leaflets are normally 45 mm (l)×23 mm (w).

*Abundance*.—On average 2 leaves per 10 cm of stem.

*Leaf color*.—Juvenile upper Yellow-Green Group N144A. Juvenile lower Yellow-Green Group N144A. Mature upper Yellow-Green Group 146A. Mature lower Yellow-Green Group 146A.

*Stipules*.—Absent.

*Petioles*.—Size: Normally 50 mm in length by 2 mm diameter. Texture: Smooth. Color: Greyed-Orange Group 173A.

*Petioloule*.—Size: Normally 20 mm in length by 2 mm diameter. Texture: Smooth. Color: Greyed-Orange Group 173A.

*Leaflet shape*.—Generally elliptic. The base is rounded. The apex is acute.

*Margin*.—Entire.

*Surface*.—The upper side is smooth. The lower side is smooth.

*Thickness*.—Average.

*Glossiness*.—Moderately glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo100', substantially as described and illustrated, due to its abundant light blue flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

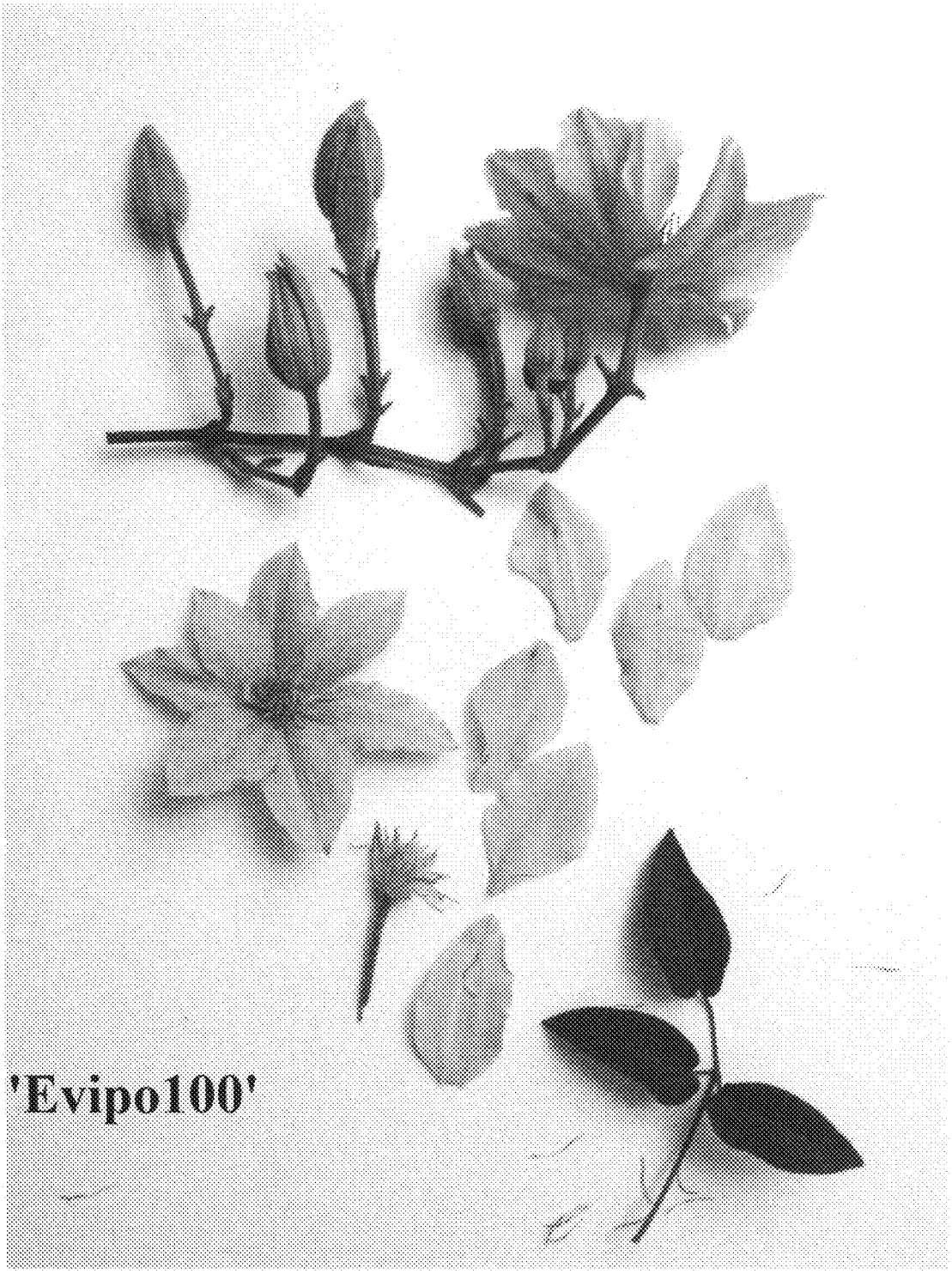
'Evipo100'